United States Patent
Yoshioka et al.

(10) Patent No.: US 6,242,624 B1
(45) Date of Patent: Jun. 5, 2001

(54) METHOD FOR MAKING ALKANOL-OR ALKANE-SULFONE PLUMBATE

(75) Inventors: Junichiro Yoshioka, Yokohama; Hiroaki Inoue, Tokyo; Kanji Ohno, Sagamihara; Akiji Sekiguchi, Tokyo, all of (JP)

(73) Assignee: Ebara Corporation, Tokyo (JP)

( * ) Notice: Subject to any disclaimer, the term of this patent is extended or adjusted under 35 U.S.C. 154(b) by 0 days.

(21) Appl. No.: 09/568,959

(22) Filed: May 11, 2000

(30) Foreign Application Priority Data

May 11, 1999 (JP) .................................................. 11-129779

(51) Int. Cl.[7] ........................................................ C07F 7/24
(52) U.S. Cl. ................................................................ 556/85
(58) Field of Search ................................................. 556/85

(56) References Cited

U.S. PATENT DOCUMENTS

| | | | |
|---|---|---|---|
| 4,116,873 | * 9/1978 | De Vries | 252/33 |
| 4,138,351 | * 2/1979 | Gilliams et al. | 252/62.1 L |
| 5,162,555 | * 11/1992 | Remmers et al. | 556/85 |
| 5,618,404 | * 4/1997 | Okuhama et al. | 205/445 |

* cited by examiner

Primary Examiner—Porfirio Nazario-Gonzalez
(74) Attorney, Agent, or Firm—Wenderoth, Lind & Ponack, L.L.P.

(57) ABSTRACT

An object of the present invention is to provide a method for obtaining alkanol-sulfonic or alkane-sulfonic plumbates efficiently by improving the solubility of lead oxide compound such as $Pb_3O_4$ or $PbO_2$ that are difficult to dissolve in alkanol-sulfonic acid or alkane-sulfonic acid.

The method involves reacting difficult-to-dissolve lead oxide compound with a solution of alkanol-sulfonic or alkane-sulfonic acid, wherein a phenol compound is contained in the solution.

5 Claims, No Drawings

METHOD FOR MAKING ALKANOL-OR ALKANE-SULFONE PLUMBATE

BACKGROUND OF THE INVENTION

1. Field of the Invention

The present invention relates in general to methods for making akanol- or alkane-sulfone plumbates used for lead plating and solder plating applications, and relates in particular to a method for making alkanol- or alkane-sulfone plumbates using lead oxide compounds as feed material, which have been regarded as difficult to dissolve in alkanol-sulfonic acid or alkane-sulfonic acid.

2. Description of the Related Art

For work involving lead plating and solder plating containing lead, acidic plating solutions based on alkanol-sulfonic acid or alkane-sulfonic acid are used. The alkanol-sulfonic or alkane-sulfonic plumbates are usually used as source of lead in such cases.

Conventionally, alkanol-sulfonic or alkane-sulfonic plumbates, in particular low α-rays radiation alkanol-sulfonic or alkane-sulfonic plumbates are generally made by reacting alkanol-sulfonic acid or alkane-sulfonic acid on metallic lead. However, it is desirable to make such materials by using naturally existing lead oxides.

Particularly, it is known in recent years that a-rays radiation emitted from lead contained in soldered products causes malfunction of electronic devices. Since then, alkanol-sulfonic or alkane-sulfonic plumbates have been made by using materials of low α-rays radiation lead oxide compounds. However, the volume of production of low radiation lead compounds is relatively small, and the production is tight for supplying thereto to satisfy the demand.

On the other hand, lead oxide such as $Pb_3O_4$ and $PbO_2$ are difficult to dissolve in alkanol-sulfonic acid and alkane-sulfonic acid, and they have not been considered as feed materials for making alkanol-sulfonic or alkane-sulfonic plumbates. However, as the availability of low-radiation lead compounds becomes more difficult, there has been required for a method of making low-radiation alkanol-sulfonic or alkane-sulfonic plumbates by using such lead oxide compounds.

SUMMARY OF THE INVENTION

It is an object of the present invention to provide a method for make alkanol-sulfonic or alkane-sulfonic plumbates efficiently by improving the solubility of lead oxides such as $Pb_3O_4$ and $PbO_2$ that are difficult to dissolve in alkanol-sulfonic acid or alkane-sulfonic acid.

The present method has been derived from inventors, intense examination of methods of dissolving lead oxide compounds that have been considered to be difficult to dissolve in alkanol-sulfonic or alkane-sulfonic acid. The present invention is based on a discovery by the inventors that the presence of phenol compounds plays a large role in dissolving the difficult-to-dissolve lead oxide compounds.

The present method is based on making alkanol-sulfonic or alkane-sulfonic plumbates by reacting difficult-to-dissolve lead oxide compound with a solution of alkanol-sulfonic or alkane-sulfonic acid, wherein a phenol compound is contained in the solution.

According to the present invention, it is easily possible to obtain alkanol-sulfonic or alkane-sulfonic plumbates efficiently from the difficult-to-dissolve lead oxide compounds at good yield.

In particular, by using the present method, it is possible to provide alkanol-sulfonic or alkane-sulfonic plumbates using the difficult-to-dissolve lead oxide compounds that have low α-rays radiation property as feed material for solder plating. Thus the solder plating does not cause mulfunction of electron devices being soldered thereby.

The above and other objects, features, and advantages of the present invention will become apparent from the following description when taken in conjunction with the accompanying drawings which illustrate preferred embodiments of the present invention by way of example.

DETAILED DESCRIPTION OF THE PREFERRED EMBODIMENTS

To practice the present invention, the difficult-to-dissolve lead oxide compounds should be dissolved in an aqueous solution of alkanol-sulfonic or alkane-sulfonic acid containing a phenol compound.

First, the difficult-to-dissolve lead oxide compounds as a starting material include trilead tetroxide ($Pb_3O_4$) and lead dioxide ($PbO_2$). Such difficult-to-dissolve lead oxide compounds may be the regular type that has high α-rays radiation property. However, it is more preferable to use low α-rays radiation property materials that are currently in short supply. For example, those with α-rays radiation property of less than 0.3 $C/cm^2$ h are prefferable.

The phenol compounds that are used in aqueous solution of alkanol-sulfonic or alkane-sulfonic acid include catechol, o-aminophenol and others. Such phenol compounds are already known as additives in lead plating, however it has not yet been reported that they are used for dissolving difficult-to-dissolve lead oxide compounds into aqueous solution of alkanol-sulfonic or alkane-sulfonic acid.

On the other hand, alkanol-sulfonic acid utilized in the present invention may include isethionic acid. Also, alkane-sulfonic acid includes methansulfonic acid, ethansulfonic acid and so on. The concentration of alkanol-sulfonic or alkane-sulfonic acid may be preferable between 100 to 300 g/L (liter).

Further, the volume of phenol compound in aqueous solution of alkanol-sulfonic or alkane-sulfonic acid is preferably between 1/10–1/1000 mol with respect to the alkanol-sulfonic or alkane-sulfonic acid.

The present method involves the steps of adding the difficult-to-dissolve lead oxide compounds in an aqueous solution of alkanol-sulfonic or alkane-sulfonic acid containing a phenol compound, stirring the solution for about 30 minutes to one hour at room temperature to dissolve the compounds. As the dissolution reaction proceeds, the temperature rises to about 50 or 60° C., but there is no particular need to cool the solution, and it is acceptable to let the reaction proceed.

By carrying out the steps outlined above, difficult-to-dissolve lead oxide compounds are completely dissolved in alkanol-sulfonic or alkane-sulfonic acid, therefore, the solution can be filtered and processed according to regular methods to obtain alkanol-sulfonic or alkane-sulfonic plumbates.

The present invention will be demonstrated in detail by examples given below, however it should be noted that the present invention is not limited by the specific details in the examples.

EXAMPLE 1

Methansulfonic acid 300 g, catechol 8 g, and trilead tetroxide pellets ($Pb_3O_4$) 170 g were added to 1030 g of water, and the mixture was stirred for 60 minutes. The solution temperature was 25° C. initially, but it rose up to 50° C. When the pellets were dissolved completely in a solution, volume of 1200 mL (milli-liter) of the liquid is obtained. The resulting liquid was a transparent yellowish solution and its specific gravity was 1.224.

Analysis result of the solution showed that it contained 125.5 g/L (liter) of lead, and the yield of methane-sulfonic plumbate computed from the amount of lead contained was 97.7%

EXAMPLE 2

Methansulfonic acid 300 g, catechol 4 g, and trilead tetroxide pellets ($Pb_3O_4$) 170 g were added to 1030 g of water, and the mixture was stirred for 50 minutes. The solution temperature was 25° C. initially, but it rose up to 50° C. When the pellets are dissolved completely in a solution, volume of 1200 mL (milli-liter) of the liquid was obtained. The resulting liquid was a transparent yellowish solution and its specific gravity was 1.223.

Analysis result of the solution showed that it contained 122 g/L (liter) of lead, and the yield of methane sulfonic plumbate computed from the amount of lead contained was 95.0%.

COMPARISON EXAMPLE

Methansulfonic acid 300 g and trilead tetroxide pellets ($Pb_3O_4$) 170 g were added to 1030 g of water, and the mixture was stirred for 60 minutes. The solution temperature was 25° C. initially, but it rose up to 50° C. After stirring the solution of volume of 1150 mL (milli liter) for 60 minutes, the resulting liquid was a yellowish milky solution and its specific gravity was 1.184.

The solution contained 85 g/L (liter) of lead, and the yield of methane sulfone plumbate computed from the amount of lead contained was 63.4%.

Although certain preferred embodiments of the present invention have been shown and described in detail, it should be understood that various changes and modifications may be made therein without departing from the scope of the appended claims.

What is claimed is:

1. A method for making alkanol-sulfonic or alkane-sulfonic plumbates, comprising:

reacting difficult-to-dissolve lead oxide compound with a solution of alkanol-sulfonic or alkane-sulfonic acid, wherein a phenol compound is contained in the solution.

2. A method according to claim 1, wherein said difficult-to-dissolve lead oxide compound includes trilead tetroxide ($Pb_3O_4$) or lead dioxide ($PbO_2$).

3. A method according to claim 1, wherein said difficult-to-dissolve lead oxide compound has a property of emitting α-rays radiation not more than 0.3 $C/cm^2$ h.

4. A method according to claim 1, wherein said phenol compound includes catechol or o-aminophenol.

5. A method according to claim 1, wherein said phenol compound is contained in the solution at a concentration of $1/10$ to $1/1000$ mol with respect to an alkanol-sulfonic acid or an alkane-sulfonic acid.

* * * * *